United States Patent [19]
Lesko

[11] Patent Number: 5,643,234
[45] Date of Patent: Jul. 1, 1997

[54] OSTOMY BAG WITH MULTI-STAGE FILTER

[75] Inventor: Marc Lesko, Jackson, N.J.

[73] Assignee: E. R. Squibb & Sons, Inc., Princeton, N.J.

[21] Appl. No.: 382,475

[22] Filed: Feb. 1, 1995

[51] Int. Cl.⁶ ............................................. A61F 5/44
[52] U.S. Cl. ............................................. 604/333; 604/338
[58] Field of Search ................................ 604/317, 332, 604/333, 338, 342, 340, 341, 324, 335

[56] References Cited

U.S. PATENT DOCUMENTS

| | | | |
|---|---|---|---|
| 4,957,522 | 9/1990 | Bressell | 604/333 |
| 5,074,851 | 12/1991 | Pless et al. | 604/333 |
| 5,250,042 | 10/1993 | Torgalker et al. | 604/333 |
| 5,306,264 | 4/1994 | Ferguson et al. | 604/333 |
| 5,352,316 | 10/1994 | Steer | 604/333 |
| 5,370,638 | 12/1994 | Rekeyes | 604/333 |
| 5,417,678 | 5/1995 | Baumann et al. | 604/333 |
| 5,468,235 | 11/1995 | La Gro | 604/333 |

FOREIGN PATENT DOCUMENTS

| | | | |
|---|---|---|---|
| 2149306 | 6/1985 | United Kingdom | 604/333 |

*Primary Examiner*—Mark O. Polutta
*Attorney, Agent, or Firm*—Stuart E. Krieger

[57] ABSTRACT

The ostomy bag includes a multi-stage filter system that provides contamination protection for a deodorizing filter in the system. The multi-stage filter system also includes protection elements that are impassable to semi-liquid waste material but permit passage of gaseous waste. The protection elements are located such that gaseous waste must pass through the protection elements before it passes through the deodorizing filter. In one embodiment of the invention, the protection elements include a fluid and gas-impermeable cover layer with fluid bypass ports. The fluid and gas-impermeable cover layer is followed by a barrier filter that restricts passage of semi-liquid waste material. The barrier filter is followed by a liquid-impermeable membrane that prevents passage of liquid. The liquid-impermeable membrane is followed by a moisture-absorbent pad that is adjacent the deodorizing filter. The moisture-absorbent pad absorbs moisture condensate that may progress as vapor through the liquid-impermeable membrane. Thus semi-liquid waste cannot contact the deodorizing filter, since it cannot bypass the protection elements to reach the deodorizing filter.

10 Claims, 3 Drawing Sheets

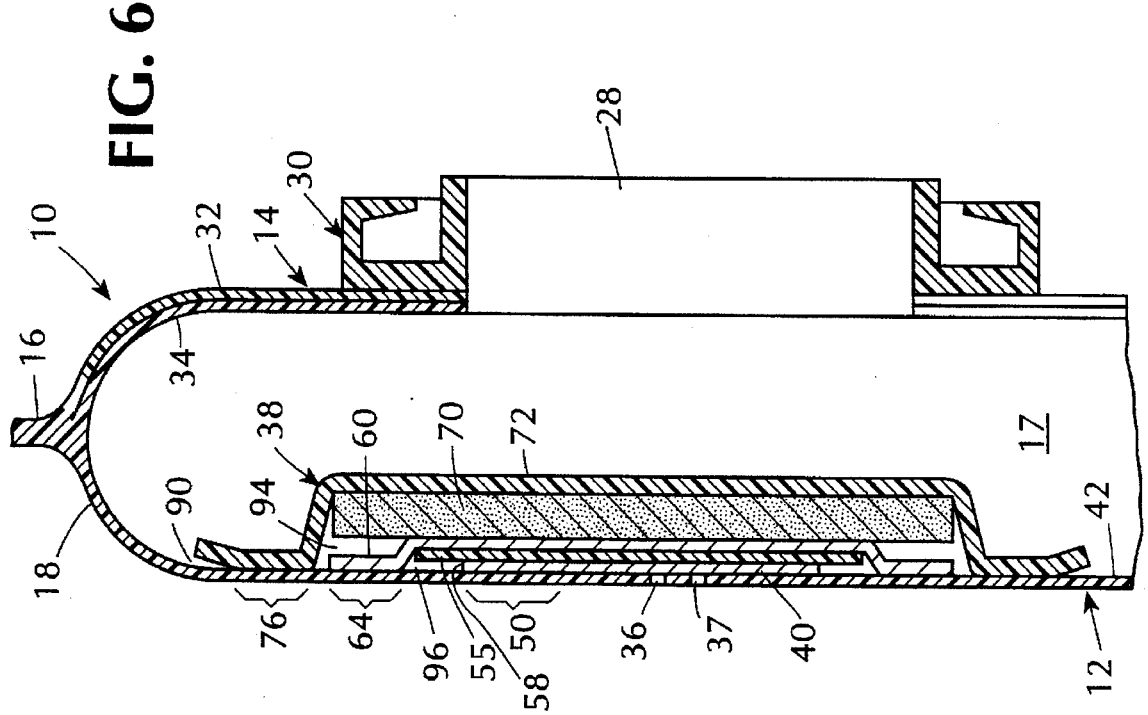
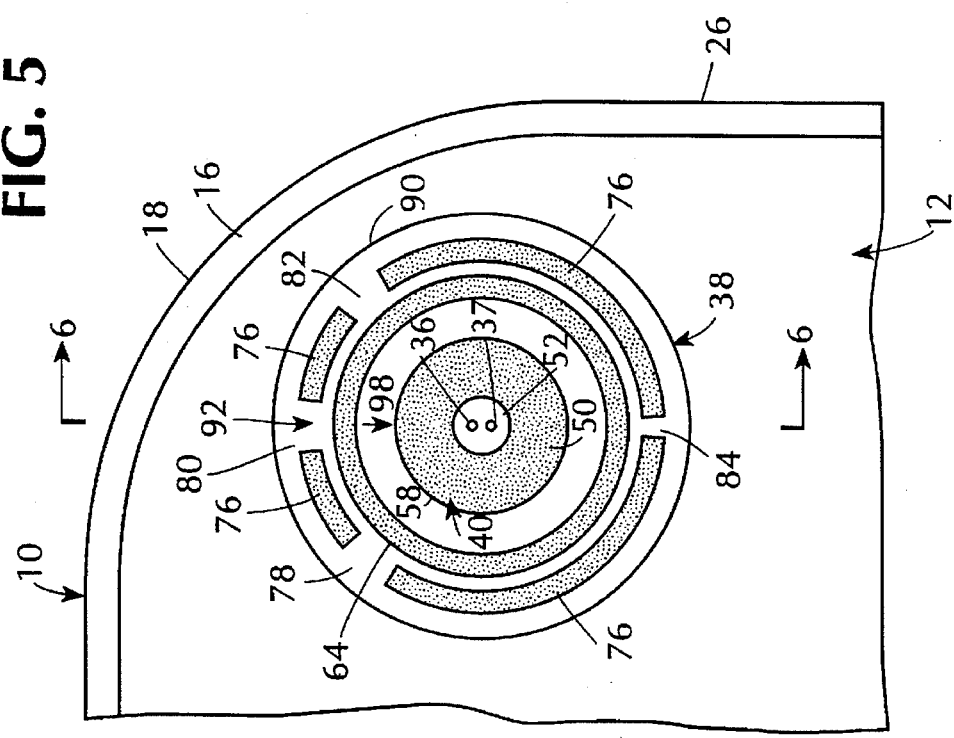

OSTOMY BAG WITH MULTI-STAGE FILTER

BACKGROUND OF THE INVENTION

This invention is directed to ostomy bags and more particularly to an ostomy bag with a novel multi-stage filter that resists contact contamination by semi-liquid waste collected in the bag.

Gases emitted from the stoma into an ostomy bag and gases that issue from waste material confined in the bag are usually deodorized before being evacuated from the bag. A deodorizing filter is generally located adjacent a gas outlet opening in the bag to ensure that the outward flow of gas from the bag passes through the deodorizing filter.

Most ostomy bags are normally worn for several days before the deodorizing capability of the filter begins to lose effectiveness. An ineffective or exhausted deodorizing filter can be replaced if the bag has provision for replaceable filters as in ostomy bags of U.S. Pat. No. 5,085,652. If there is no provision for filter replacement as in the ostomy bag of U.S. Pat. No. 5,074,851, the entire bag is often replaced when the deodorizing filter is no longer an effective deodorizer.

If the deodorizing filter is inadvertently contaminated by contact with waste material that accumulates in the bag, it may be desirable to replace the disposable bag immediately. Waste material contact with a deodorizing filter can occur as a result of physical activity by the wearer that, for example, shifts the contents of the bag toward the deodorizing filter, especially if such waste material is of a liquid or semi-liquid consistency.

Contact of the deodorizing filter with semi-liquid waste material will often clog the filter, thereby preventing adequate deodorization and evacuation of waste gas. Whenever a deodorizing filter is contaminated by contact with semi-liquid waste material and such contamination impedes the function of the deodorizing filter, the filter or bag should be replaced as soon as possible. The need for unexpected or accelerated replacement of deodorizing filters and/or ostomy bags because of contact contamination by waste is often at an inconvenience to the wearer.

Ostomy bag deodorizing filter contamination from contact with semi-liquid waste also commonly occurs when an individual is asleep or reclining and the ostomy bag is in a relatively horizontal orientation. In such instances of filter contamination, gas pressure is likely to build up in the bag because of a diminished rate of gas evacuation due to deodorizing filter clog. Occasionally pressure buildup in the bag will overcome the seal between the bag and the bag mounting surface. Once the seal between the bag and the mounting surface is broken, leakage of gas and other contents of the bag can occur, and if such leak or seal break is not detected, it can result in offensive odors as well as the soiling of an individual's garments.

It is thus desirable to provide an ostomy bag with a multi-stage filter system that prevents semi-liquid waste material from contaminating a deodorizing element but does not inhibit evacuation of gaseous waste through the deodorizing element.

OBJECTS AND SUMMARY OF THE INVENTION

Among the several objects of the invention may be noted the provision of a novel ostomy bag, a novel ostomy bag with a protective device for a deodorizing element, a novel protective device which prevents semi-liquid waste material from contaminating the deodorizing element of an ostomy bag while permitting gaseous waste material to pass through the deodorizing element, a novel ostomy bag with a novel multi-stage filter system for gas deodorizing that enables a deodorizing element to resist contact contamination by semi-liquid waste material, and a novel method of preventing contamination of a gas deodorizing filter.

Other objects and features of the invention will be in part apparent and in part pointed out hereinafter.

In accordance with the invention, the multi-stage filter includes a gas transmissive protective device for a deodorizing element that is impassible to semi-liquid waste material. The gas transmissive protective device precedes the deodorizing element or filter such that gaseous waste must pass through the protective device before it passes through the filter.

In one embodiment of the invention, the multi-stage filter elements include a deodorization filter intended to remove odor, a moisture-absorbent pad and a liquid-impermeable microporous protection film intended to protect the deodorizing filter from moisture, a foam filter that forms a barrier to restrict passage of semi-liquid waste and liquids, and a plastic fluid-impermeable film cover that shrouds the other multi-stage filter elements.

The fluid-impermeable film cover is the first line of protection for the other elements of the multi-stage filter especially from the semi-liquid waste. The fluid-impermeable film cover is bonded to a wall of the pouch along a discontinuous bond line. The discontinuities at the line define access paths for bypassing the fluid-impermeable film cover, wherein substantially only gas flows through the succeeding elements of the multi-stage filter for eventual evacuation from the ostomy bag.

The deodorizing filter is located adjacent the gas outlet so as to precede the gas outlet relative to the flow path of gaseous waste through the deodorizing filter. Thus gaseous waste must bypass the fluid-impermeable film cover, the foam barrier filter, the liquid-impermeable microporous film and the moisture-absorbent pad before such gas passes through the deodorizing filter.

The multi-stage filter is constructed to be substantially impassible to semi-liquid waste material while permitting gaseous waste to pass through. Under this arrangement the deodorizing filter is amply protected from contact with semi-liquid waste material. The deodorizing filter, by avoiding clogging contact with semi-liquid waste material can operate for its rated life and thereby enable the ostomy bag to be used for a normal duration period before filter replacement or bag replacement is required.

The invention accordingly comprises the constructions and method hereinafter described, the scope of the invention being indicated in the claims.

DESCRIPTION OF THE DRAWINGS

In the accompanying drawings,

FIG. 5 is an enlarged fragmentary plan view of the reverse side thereof; and

FIG. 6 is a section view taken on the line 6—6 of FIG. 5; and,

Corresponding reference characters indicate corresponding parts throughout the several views of the drawings.

DETAILED DESCRIPTION OF THE INVENTION

Figure 1:
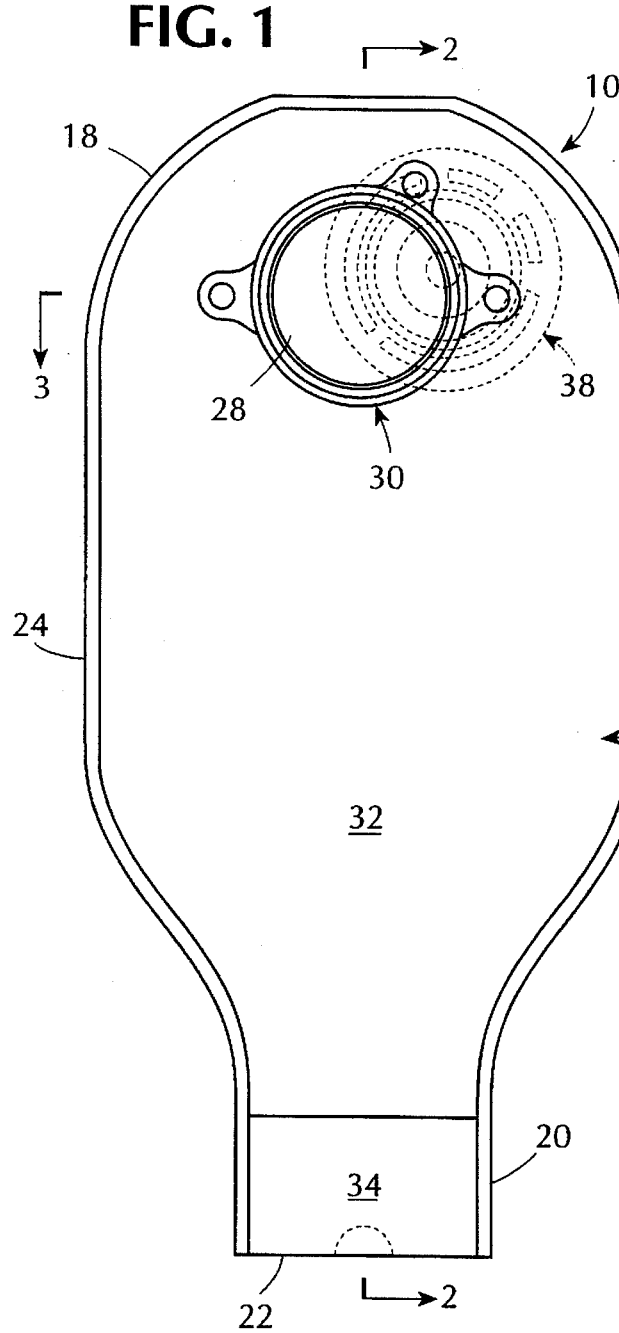
FIG. 1 is a simplified schematic plan view of one side of an ostomy bag incorporating one embodiment of the invention.

An ostomy bag incorporating one embodiment of the invention is generally indicated by the reference number 10 in FIG. 1. The ostomy bag is formed of a suitable known thermoplastic material that is gas-impermeable, flexible and expandable.

The bag 10 includes a front wall 12 that faces away from the abdomen, and a rear wall 14 that confronts the abdomen, joined together by a peripheral thermoweld 16 to define a waste collection chamber 17. The walls 12 and 14 are approximately 40 to 100 microns thick. The bag 10 further includes a top portion 18, a bottom portion 20 with a reclosable open end 22, and opposite side portions 24 and 26. A reusable clamp (not shown) is provided at the bottom portion 20 to open and close the open end 22.

Figure 2:
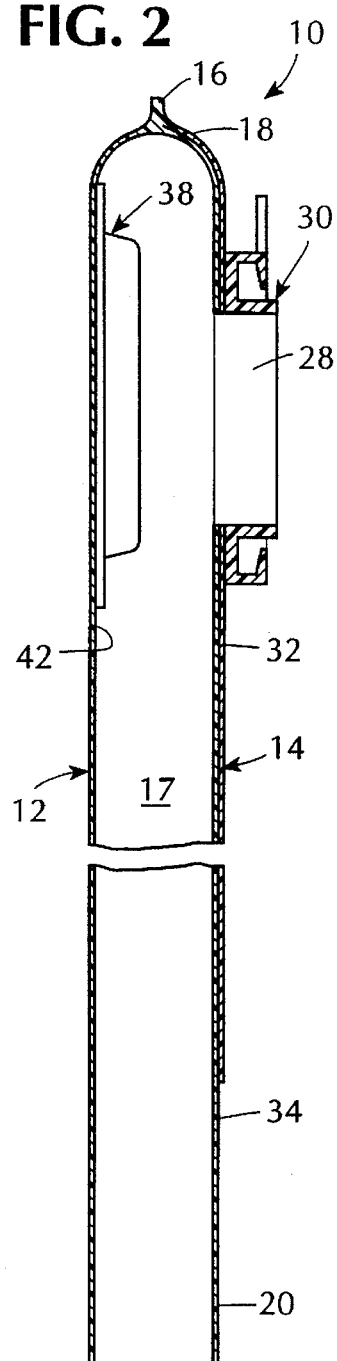
FIG. 2 is a section view taken on the line 2—2 of FIG. 1.
Figure 3:
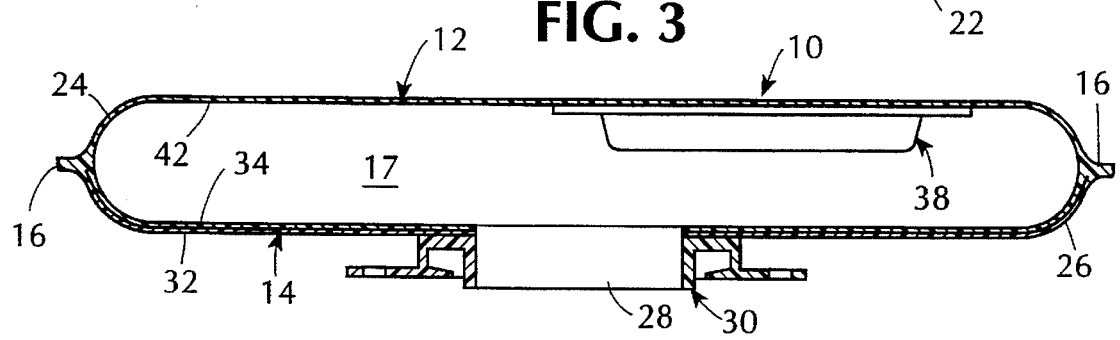
FIG. 3 is a section view taken on the line 3—3 of FIG. 1.

A stoma engagement opening 28 is formed in the rear wall 14 nearer the top portion 18 of the bag 10 than the bottom portion 20. The stoma engagement opening 28 is bordered by a known flexible plastic coupling flange 30 in the form of a ring joined to a first layer 32 of the rear wall 14 in any suitable known manner. The rear wall 14 (FIGS. 2 and 3) also includes a second layer 34. The coupling flange 30 interlocks with a known interlocking ring flange (not shown) that is provided around the stoma.

Figure 4:
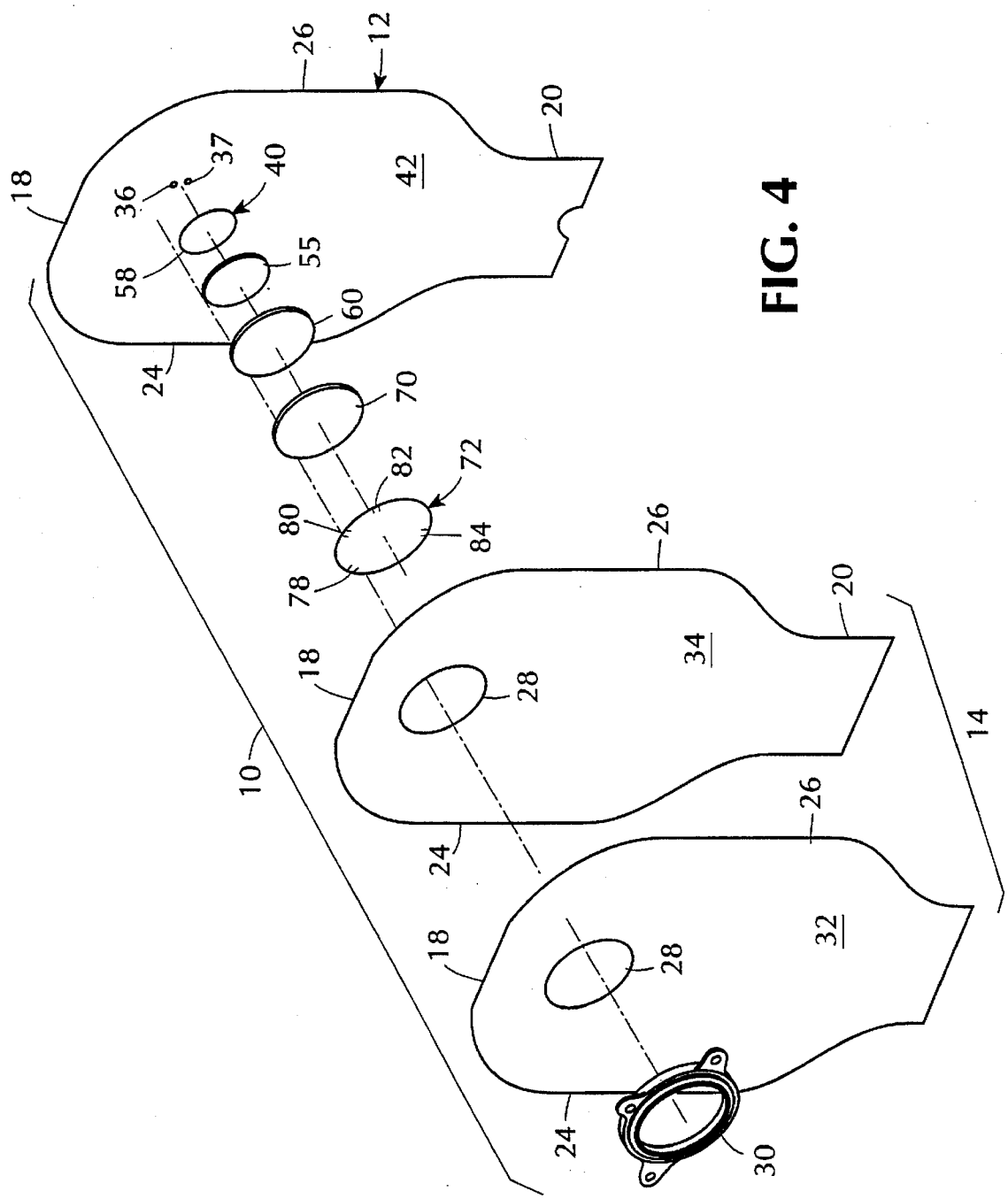
FIG. 4 is an exploded perspective view thereof.

A pair of gas evacuation openings 36, 37 (FIGS. 4, 5 and 6) of pinhole size, approximately 0.762 mm in diameter, are formed in the front wall portion 12 of the bag 10 near the top and side edges 18 and 26, offset from the stoma engagement opening 28. A bag with a single gas evacuation hole 36 is also feasible.

A multi-stage filter 38 for the bag 10 includes a generally circular deodorizing filter 40 provided at an inside surface 42 of the front wall 12 in substantial alignment with the gas evacuation openings 36 and 37. The deodorizing filter 40 is of the type sold under the designation Freudenberg Code 9347 by Freudenberg Industrial of West Yorkshire, England, and includes a filtration layer formed of polyurethane foam containing activated carbon sandwiched between opposite cover layers.

One cover layer of the deodorizing filter 40 faces an inside surface 42 of the wall 12 and is gas-permeable, being formed of micro-fine nonwoven material with a layer of hot melt adhesive. The other cover layer of the deodorizing filter 40 faces away from the wall 12 and is gas semi-permeable microporous film. Preferably the deodorizing filter 40 is approximately 23 to 26 mm in diameter and 2 to 3 mm thick.

The deodorizing filter 40 is joined at its gas-permeable cover layer to the inside surface 42 of the front wall 12 along an annular gas-impermeable bonding zone 50 (FIGS. 5 and 6). Heat is applied to a hot-melt adhesive layer at the bonding zone 50 to provide a bond width of approximately 8.6 mm. Thus a central circular unbonded area 52 (FIG. 5) of approximately 7.1 mm in diameter is defined in the gas-permeable cover layer within the confines of the bonding zone 50. The unbonded area 52 confronts the gas evacuation holes 36 and 37 in the front wall 12.

Since the opposite cover layer of the deodorizing filter 40, which faces away from the wall 12, is gas semi-permeable, gas can only enter the deodorizing filter 40 at a peripheral edge 58 of the filter 40 (FIGS. 5 and 6).

The multi-stage filter 38 also includes a superabsorbent pad 55 which is provided behind the deodorizing filter 40 to prevent moisture vapor condensate from wetting the filter 40. The pad 55 is made of acrylic water-absorbing resin and a nonwoven substrate such as supplied by Gelok Inc. of Dunbridge, Ohio under the designation Gelok 6600 A/A laminate approximately 0.4 to 0.8 mm thick. The superabsorbent pad 55 can be placed adjacent to, bonded or laminated to the deodorizing filter 40.

A further example of the superabsorbent pad 55 is the type sold under Catalog No. 202.150 by Cellosoft Company of Sweden, which contains a superabsorbent powder such as the type sold under the designation Salsorb 84 by Allied Colloid.

The multi-stage filter 38 also includes a liquid-impermeable microporous membrane or film 60 which is joined to the front wall 12 of the bag 10 at the inside surface 42 along an annular bonding zone 64 (FIGS. 5 and 6) that encircles the deodorizing filter 40 and the superabsorbent pad 55. The liquid-impermeable membrane or film 60 is formed of microporous breathable polymer film approximately 0.13 mm thick, with a plurality of microporous holes approximately 1 micron in diameter, such as supplied by Millipore Company of Bedford, Mass., under the designation Durapel. It should be noted that the film or membrane 60 can have other dimensions compatible with the objectives of the invention, so long as it has the properties of being liquid-impermeable with a plurality of microporous holes.

The multi-stage filter 38 additionally includes a protective filter 70 located behind the microporous membrane or film 60, as shown in FIG. 6. The protective filter 70 is preferably an open cell foam to form a barrier to semi-liquid waste, but not gases. The protective barrier filter 70 is approximately 3.20 mm thick, preferably formed of reticulated open cell polyurethane foam such as sold by Reilly Foam Corp. of Hartford, Conn. The protective barrier filter 70 can be of one pore size such as 25 pores per inch, or the filter 70 can be a dual layer arrangement with two pore sizes, with the second layer having approximately 45 pores per inch with a pore diameter of approximately 45 mm. The barrier filter 70 can also be formed of a hybrid foam construction layer having approximately 30 pores per inch with a pore diameter of approximately 45 mm.

The multi-stage filter 38 further includes a fluid-impermeable film wafer 72, preferably formed of plastic, such as gas-impermeable thermoplastic film of the type used to form the front and rear walls 12 and 14 of the bag 10. The film wafer 72 is approximately 3 mm thick, and is joined to the inside surface 42 of the front wall 12. The fluid-impermeable film 72 is bonded at a discontinuous annular bonding zone 76 approximately 63.5 mm inside diameter to encircle and shroud the protective barrier filter 70, the liquid-impermeable microporous membrane or film 60, the superabsorbent pad 55 and the deodorizing filter 40.

The width of the bonding zone 76 is approximately 3.2 mm and preferably four spaced discontinuities 78, 80, 82 and 84 are provided in the bonding zone 76. The discontinuities 78, 80 and 82 serve primarily as gas inlet ports and are approximately 8 mm in extent. The discontinuity 84, which is downwardly directed, also serves as a drainage port as well as an inlet port, and is approximately 3.2 mm in extent.

In operation of the ostomy bag 10, the coupling flange 30 is engaged with a ring-shaped mating coupling flange (not shown) provided around the stoma (not shown). The coupling flange engagement forms a substantially leak-tight seal between the stomal opening 28 of the bag 10 and the stoma. The open end 22 of the bottom portion 20 is clamped shut in leak-tight fashion using any suitable known releasable clamp (not shown).

With the ostomy bag 10 thus installed on a user, semi-liquid and gaseous waste material (not shown) are allowed to enter the stomal opening 28 into the collection chamber 17 defined between the front and rear walls 12 and 14 of the bag 10. The semi-liquid waste and gaseous waste accumulate in the collection chamber 17 with the gaseous waste being evacuated through the deodorizing filter 40 and the gas outlet openings 36 and 37.

Before the gaseous waste reaches the deodorizing filter 40 and the gas outlets 36 and 37, it must pass through the discontinuities 78, 80 and 82 in the bonding zone 76 of the fluid-impermeable film wafer 72. The semi-liquid waste does not clog the film wafer 72 because of the size, number and positioning of the discontinuities 78, 80, 82 and 84.

An annular peripheral edge portion 90 of the film wafer 72 is left unbonded as most clearly shown in FIG. 5, to provide an annular guideway for the gaseous waste to enter the discontinuities 78, 80, 82 and 84, as for example, along a path indicated by the arrow 92.

Referring to FIG. 5, gaseous waste from the path indicated by the arrow 92 enters a space 94 (FIG. 5) between the fluid-impermeable film wafer 72 and the liquid-impermeable microporous membrane or film 60. The space 94 is normally substantially fully occupied by the protective filter barrier 70. The foam pores or cells of the filter barrier 70 block the passage of semi-liquid waste material by providing a tortuous path that cannot be negotiated by the semi-liquid waste.

The cells of the foam filter barrier 70 also cause bubbles of fluid to form by surface tension. The bubbles of fluid cling to the foam cells and interrupt the flow of the semi-liquid waste. Body motion by the user results in an ongoing breaking and reforming of the surface tension bubbles which provides a path for the gaseous waste to travel through the filter barrier 70.

The waste gas thus passes through the protective barrier filter 70 and through the pores of the liquid-impermeable microporous membrane or film 60 into an annular peripheral space 96 that is normally substantially fully occupied by the superabsorbent pad 55 for absorbing moisture. The waste gas passes through the superabsorbent pad 55 and toward the periphery 58 of the deodorizing filter 40 in the direction indicated by the arrow 98 in FIG. 5.

Gaseous waste flows through the deodorizing filter 40 toward the central unbonded area 52 between the filter 40 and the front wall 12. The unbonded area 52 defines an evacuation zone for the waste gas to exit from the bag 10 to the outside, through the gas outlet openings 36 and 37, which align with the unbonded area 52. Under this arrangement, the deodorization filter 40 is protected by the combination of the super-moisture-absorbent pad 55, the liquid-impermeable microporous membrane or film 60, the protective barrier filter 70 that restricts passage of semi-liquid waste and the fluid-impermeable film wafer 72.

Since the multi-stage filter system 38 provides moisture and contamination protection for the deodorizing filter 40, the deodorizing filter 40 is enabled to effectively deodorize flatus during the normal period of use of the ostomy bag 10.

As will be apparent to those skilled in the art, the multi-stage filter assembly 38 is also adaptable to most types of ostomy bags including adhesive mounted bags and bags that do not have bottom openings.

Some advantages of the invention evident from the foregoing description include an ostomy bag with a multi-stage filter system that provides contamination and moisture protection for a deodorizing filter and helps assure against inadvertent premature contamination of the deodorizing filter by semi-liquid waste material accumulated in the bag. A further advantage of the ostomy bag is that the multi-stage filter system enables the user to engage in activities or body postures that may shift the contents of the bag, without fear that such activities will cause contamination of the deodorizing filter. A further advantage of the invention is that the ostomy bag can be reliably worn for its normal rated life because the deodorizing filter is not likely to be prematurely contaminated by semi-liquid waste material.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An ostomy bag for holding body waste that passes through a stoma comprising, a) an envelope formed of flexible plastic sheet material defining a waste collection chamber for body waste that includes gaseous and semi-liquid waste material, said envelope having interior surface portions and a top end portion, b) a waste inlet opening formed in said envelope proximate said top end portion, said waste inlet opening being of predetermined size and including means for fitting said opening around a stoma, c) gas outlet means formed in said envelope proximate said top end portion and spaced from said waste inlet opening, d) a deodorizing filter joined to said envelope in alignment with said gas outlet means for deodorizing gaseous waste material before said gaseous waste material exits from said bag through said gas outlet means, and e) means for protecting said deodorizing filter from contact by semi-liquid waste material, and for permitting the flow of gaseous waste, and for preventing the flow of semi-liquid waste, said protection means being located in said envelope to precede the deodorizing filter such that the gaseous waste must pass through said protection means before it passes through said deodorizing filter, said protection means comprising, (1) a pad containing moisture absorbent polymer adjacent said deodorizing filter to absorb moisture condensation and prevent such condensate from reaching said deodorizing filter, said moisture-absorbent pad being gas-transmissible to enable gaseous waste to pass to said deodorizing filter, (2) a liquid-impermeable membrane adjacent said moisture-absorbent pad to prevent liquid from passing through said liquid-impermeable membrane to said moisture-absorbent pad, said liquid-impermeable membrane being gas-transmissible to enable gaseous waste to pass to said moisture-absorbent pad, (3) a barrier filter for semi-liquid waste adjacent said liquid-impermeable membrane for providing a tortuous path for semi-liquid waste to substantially prevent passage of said semi-liquid waste through said barrier filter to said liquid-impermeable membrane, said barrier filter being gas-transmissible to enable gaseous waste to pass to said liquid-impermeable membrane, and (4) a fluid and gas-impermeable cover layer adjacent said barrier filter to cover said barrier filter, said liquid-impermeable membrane, said moisture-absorbent pad and said deodorizing filter, said fluid and gas-impermeable cover layer being provided with fluid entry means for permitting gaseous waste to bypass the fluid and gas-impermeable cover layer to pass to said barrier filter.

2. The ostomy bag as claimed in claim 1, wherein said moisture-absorbent pad covers said deodorizing filter.

3. The ostomy bag as claimed in claim 2, wherein said moisture-absorbent pad shrouds said deodorizing filter.

4. The ostomy bag as claimed in claim 2, wherein said fluid and gas-impermeable cover layer is joined to said envelope by a discontinuous bond, such that discontinuities in said bond define said fluid entry ports.

5. The ostomy bag as claimed in claim 4, wherein one of said fluid entry ports is positioned downwardly to also function as a drain port.

6. The ostomy bag as claimed in claim 1 wherein the said moisture-absorbent pad is laminated to said deodorizing filter.

7. The ostomy bag as claimed in claim 1, wherein said gas outlet means comprise at least one hole.

8. The ostomy bag as claimed in claim 1, wherein said gas outlet means comprise two holes.

9. The ostomy bag as claimed in claim 8, wherein said holes have a diameter of approximately 0.762 mm.

10. The ostomy bag as claimed in claim 1, wherein said barrier filter comprises an open cell foam material.

\* \* \* \* \*